United States Patent
Mueller et al.

(10) Patent No.: US 10,358,709 B2
(45) Date of Patent: Jul. 23, 2019

(54) MAGNESIUM-ZINC-CALCIUM ALLOY, METHOD FOR PRODUCTION THEREOF, AND USE THEREOF

(71) Applicant: BIOTRONIK AG, Buelach (CH)

(72) Inventors: Heinz Mueller, Diedrichshagen (DE); Peter Uggowitzer, Ottenbach (CH); Joerg Loeffler, Greifensee (CH)

(73) Assignee: BIOTRONIK AG, Buelach (CH)

( * ) Notice: Subject to any disclaimer, the term of this patent is extended or adjusted under 35 U.S.C. 154(b) by 162 days.

(21) Appl. No.: 14/395,713

(22) PCT Filed: Jun. 24, 2013

(86) PCT No.: PCT/EP2013/063111
§ 371 (c)(1),
(2) Date: Oct. 20, 2014

(87) PCT Pub. No.: WO2014/001241
PCT Pub. Date: Jan. 3, 2014

(65) Prior Publication Data
US 2015/0129091 A1    May 14, 2015

Related U.S. Application Data

(60) Provisional application No. 61/664,274, filed on Jun. 26, 2012.

(51) Int. Cl.
| | |
|---|---|
| C22F 1/06 | (2006.01) |
| C22C 23/04 | (2006.01) |
| A61L 27/04 | (2006.01) |
| A61L 27/58 | (2006.01) |
| A61L 31/02 | (2006.01) |
| A61L 31/14 | (2006.01) |
| C22C 1/02 | (2006.01) |

(52) U.S. Cl.
CPC .............. C22F 1/06 (2013.01); A61L 27/047 (2013.01); A61L 27/58 (2013.01); A61L 31/022 (2013.01); A61L 31/148 (2013.01); C22C 1/02 (2013.01); C22C 23/04 (2013.01); A61L 2430/02 (2013.01); A61L 2430/12 (2013.01)

(58) Field of Classification Search
CPC ......... A61L 2430/12; C22C 23/04; C22F 1/06
USPC ........................................................ 148/538
See application file for complete search history.

(56) References Cited

U.S. PATENT DOCUMENTS

| | | | |
|---|---|---|---|
| 3,320,055 A | 5/1967 | Foerster | |
| 5,055,254 A | 10/1991 | Zuliani | |
| 5,698,158 A | 12/1997 | Lam et al. | |
| 8,518,102 B2 | 8/2013 | Kitaoka | |
| 9,072,618 B2 | 7/2015 | Doerr et al. | |
| 9,561,308 B2 | 2/2017 | Schaffer | |
| 9,593,397 B2 | 3/2017 | Imwinkelried et al. | |
| 9,677,151 B2 | 6/2017 | Eth | |
| 2008/0031765 A1 | 2/2008 | Gerold et al. | |
| 2009/0171452 A1 | 7/2009 | Yamamoto et al. | |
| 2010/0075162 A1 | 3/2010 | Yang et al. | |
| 2011/0054629 A1 | 3/2011 | Seok et al. | |
| 2011/0076178 A1 | 3/2011 | Somekawa et al. | |
| 2011/0192500 A1 | 8/2011 | Uggowitzer et al. | |
| 2011/0315282 A1 | 12/2011 | Somekawa et al. | |
| 2012/0035740 A1 | 2/2012 | Koo et al. | |
| 2012/0095548 A1 | 4/2012 | Gregorich et al. | |
| 2012/0269673 A1 | 10/2012 | Koo et al. | |
| 2013/0039805 A1 | 2/2013 | Somekawa et al. | |
| 2013/0131814 A1 | 5/2013 | Koo et al. | |
| 2013/0144290 A1 | 6/2013 | Schiffl | |
| 2014/0065009 A1 | 3/2014 | Imwinkelried et al. | |
| 2014/0261911 A1 | 9/2014 | Imwinkelried et al. | |
| 2015/0047756 A1 | 2/2015 | Washio et al. | |
| 2015/0080938 A1 | 3/2015 | Groff | |
| 2015/0080998 A1 | 3/2015 | Mueller et al. | |
| 2015/0119995 A1 | 4/2015 | Mueller et al. | |
| 2015/0129091 A1 | 5/2015 | Mueller et al. | |
| 2015/0129092 A1 | 12/2015 | Mueller et al. | |
| 2016/0022876 A1 | 1/2016 | Imwinkelried et al. | |

FOREIGN PATENT DOCUMENTS

| | | |
|---|---|---|
| CN | 1743486 A | 3/2006 |
| CN | 1792383 A | 6/2006 |
| CN | 1792384 A | 6/2006 |
| CN | 101629260 A | 1/2010 |
| CN | 101658691 | 3/2010 |
| CN | 101308105 B | 8/2010 |
| CN | 101899600 A | 12/2010 |
| CN | 102312144 | 1/2012 |

(Continued)

OTHER PUBLICATIONS

Abstract of English translation of CN 1792383A, Jun. 2006.*
NPL-2: Heublein et al, Bio-corrosion of Mg alloys: a new principle in cardiovascular implant technology? Heart 2003: 89, pp. 651-656.*
Sun, Yu, et al., "Preparation and characterization of a new biomedical MgZnCa alloy", Materials and Design, vol. 34, Jul. 23, 2011, pp. 58-64.
Xie, Yang, State Intellectual Property Office of the People's Republic of China Notification of the First Office Action, Application No. 201380022716.5, dated Mar. 3, 2016, 11 pages.
Chen, Ji-Hua, et al., "Microstructural stability and mechanical properties of Mg—Zn—Al alloys", Hunan-Daxue-Xuebao / Ziran-Kexue-Ban =Journal of Hunan University/ Hunan Daxue Zhuban, vol. 34, No. 1, Jan. 1, 2007, pp. 47-51.

(Continued)

*Primary Examiner* — Jie Yang
(74) *Attorney, Agent, or Firm* — Greer, Burns & Crain, Ltd.; Steven P. Fallon

(57) ABSTRACT

A magnesium alloy includes 3 to 7.0% Zn, 0.001 to 0.5% Ca, the remainder being magnesium containing impurities, which promote electrochemical potential differences and/or the formation of intermetallic phases, in a total amount of no more than 0.005 of Fe, Si, Mn, Co, Ni, Cu, Al, Zr and P, wherein the alloying elements are selected from the group of the rare earths having the ordinal numbers 21, 39, 57 to 71 and 89 to 103 in a total amount of no more than 0.001% by weight.

20 Claims, No Drawings

(56) References Cited

FOREIGN PATENT DOCUMENTS

| | | |
|---|---|---|
| DE | 1483204 | 10/1969 |
| DE | 102006060501 A1 | 6/2008 |
| DE | 102010027532 B4 | 6/2014 |
| EP | 0295397 A1 | 12/1988 |
| EP | 1959025 A1 | 8/2008 |
| EP | 2295613 A1 | 3/2011 |
| EP | 2384725 A1 | 11/2011 |
| EP | 2085100 B1 | 1/2015 |
| JP | 02047238 | 2/1990 |
| JP | 07018364 | 1/1995 |
| JP | H11502565 | 3/1999 |
| JP | 2010163635 A | 7/2010 |
| JP | 2010529288 | 8/2010 |
| JP | 2012082474 | 4/2012 |
| RU | 2098506 | 12/1997 |
| RU | 2437949 | 12/2011 |
| WO | 9626297 | 8/1996 |
| WO | 1997040201 A1 | 10/1997 |
| WO | 2004013364 | 2/2004 |
| WO | 2005108634 A1 | 11/2005 |
| WO | 2007058276 | 5/2007 |
| WO | 2008016150 | 2/2008 |
| WO | 2009/147861 A1 | 12/2009 |
| WO | 2009148093 | 12/2009 |
| WO | 2010082669 | 7/2010 |
| WO | 2011051424 | 5/2011 |
| WO | 2011114931 A | 9/2011 |
| WO | 2012003522 | 1/2012 |
| WO | 2013107644 | 7/2013 |
| WO | 2014001321 | 1/2014 |
| WO | 2014159328 | 10/2014 |

OTHER PUBLICATIONS

Friedrich, Horst, E., et al., "Magnesium Technology", Jan. 1, 2006 (Jan. 1, 2006), Springer, Berlin Heidelberg New York, pp. p. 231-232; p. 289-301; p. 308-315.
Geis-Gerstorfer, J., et al., "Blood triggered corrosion of magnesium alloys", Materials Science and Engineering B, 176, (2011), pp. 1761-1766.
He, Youlian, et al., "Production of Very Fine Grained Mg—3%Al—1%Zn Alloy by Continuous Extrusion Forming (CONFORM)", Advanced Engineering Materials, 12, No. 9, (2010), pp. 843-847.
Jin, Li, et al., "Mechanical properties and microstructure of AZ31 Mg alloy processed by two-step equal channel angular extrusion", Materials Letters, 59, (2005), pp. 2267-2270.
Kammer, Catrin, et al., "Magnesium Taschenbuch", Aluminium-Verlag, Duesseldorf (2000), pp. 156-161.
Kim, Ye-Lim, et al., "Effect of Al Addition on the Precipitation Behavior of a Binary Mg—Zn", Kor. J. Mater. Res., vol. 22, No. 3, (2012), pp. 111-117.
Li Xuesong, et al., "Microstructure, mechanical properties and corrosion behavior of Mg—1Zn—0.5Ca alloy", Advanced Materials Research, Trans Tech Publications Ltd., vol. 311-313, Jan. 1, 2011, pp. 1735-1740.
Liu, Qiang, et al., "Influences of Al on Microstructures and Properties of Mg—6Zn Alloys", Kuangye-Gongcheng = Mining and Metallurgical Engineering, vol. 25, No. 5, Oct. 1, 2005, pp. 74-76.
Martienssen, Werner, et al, "Springer Handbook of Condensed Matter and Materials Data—Part 3.1", Springer-Verlag Berlin Heidelberg, New York, (2005), pp. 160-170 and cover pages (23 pages).
Oh, J.C.; et al., "TEM and 3DAP characterization of an age-hardened Mg—Ca—Zn alloy", Scripta Materialia, vol. 53, No. 6, Sep. 1, 2005, pp. 675-679.
Oh-Ishi, K., et al., "Age-hardening response of Mg-0.3 at.%Ca alloys with different Zn contents," Materials Science and Engineering, A: vol. 526, Nos. 1-2, Nov. 25, 2009, pp. 177-184.
Oh-Ishi, K., et al., "Influence of Zn additions on age hardening response and microstructure of Mg-0.3at.% Ca alloys", Magnesium Technology 2010, "Proceedings of a Symposium Held During [the] TMS Annual Meeting & Exhibition," Jan. 1, 2010, pp. 517-520.
Schuetze, Michael, et al., "Fundamentals of High Temperature Corrosion", Materials Science and Technology, WILEY-VCH Verlag GmbH, 2000, pp. 67-129.
Somekawa, H., et. al., "High strength and fracture toughness balance on the extruded Mg—Ca—Zn alloy", Materials Science and Engineering: A, vol. 459, Nos. 1-2, Jun. 25, 2007, pp. 366-370.
Song, G., et al., "Corrosion of Non-Ferrous Alloys. III. Magnesium Alloys", Materials Science and Technology, WILEY-VCH Verlag GmbH, 2000, pp. 131-171.
Wang, Xi-Shu, et al., "Effect of equal channel angular extrusion process on deformation behaviors of Mg—3Al—Zn alloy", Materials Letters, 62, (2008), pp. 1856-1858.
Yang, M.B., et al., "Comparison of as-cast microstructures and solidification behaviours of Mg—Zn—Al ternary magnesium alloys with different Zn/Al mass ratios," Advanced Materials Research, Trans Tech Publications Ltd., vol. 548, Jan. 1, 2012, pp. 321-327.
Zhang, B.P., et al., "Enhanced mechanical properties in fine-grained Mg—1.0Zn—0.5Ca alloys prepared by extrusion at different temperatures", Scripta Materialia, vol. 63, No. 10, Nov. 1, 2010, pp. 1024-1027.
Zou, H., et al., "Effects of Nd on the Microstructure and Mechanical Property of ZA52 Alloy", Materials Science Forum, vols. 488-489, (2005), pp. 161-164.
Zou, H., et al., Effects of microstructure on creep behavior of Mg—5%Zn—2%Al(—2%Y) alloy, Trans. Nonferrous Met. Soc. China, vol. 18, No. 3, (Jun. 2008), pp. 580-587.
Radeck, Stephanie, "International Search Report and Written Opinion of the International Searching Authority", Patent Cooperation Treaty Application PCT/EP2013/063253, European Patent Office as International Search Authority, Search Completed Sep. 26, 2013, International Search Report dated Oct. 4, 2013, 13 pages.
Radeck, Stephanie, "International Search Report" Patent Cooperation Treaty Application No. PCT/EP2013/062876, European Patent Office as International Search Authority, dated Oct. 16, 2013, 5 pages.
Wang, Haining, "Notification of the First Office Action", Chinese Patent Application 201380022714.6, dated Mar. 9, 2016, 7 pages.
Hillis et al., "Compositional Requirements for Quality Performance with High Purity," International Magnesium Association Meeting; 55th, International Magnesium Association, (1998), pp. 74-81.
JP Office Action for Application No. 2015519055, dated Jun. 1, 2017.
Kammer, Catrin, et al., "Magnesium Taschenbuch", Aluminium-Verlag, Duesseldorf (2000), pp. 156-161 (English language machine translation).
Kannan et al., Evaluating the stress corrosion crackihnhg susceptibility of Mg—Al—Zn alloy in modified-simulated body fluid for orthopaedic implant application, Scripta Materialia, 59 (2008) pp. 175-178.
Kawamura, Yuji et al. "Office Action" Japanese Patent Application No. 2015-518992, dated May 30, 2017 (15 pages).
Radeck, Stephanie, "International Search Report and Written Opinion of the International Searching Authority", Patent Cooperation Treaty Application PCT/EP2013/063110, European Patent Office as International Search Authority, Search Completed Oct. 1, 2013, International Search Report dated Dec. 2, 2013, 10 pages.
Radeck, Stephanie, "Office Action" for EP Office Action Application No. 13730893.8, dated Apr. 19, 2017.
Radeck, Stephanie, "Office Action" for EP Office Action Application No. 13731134.6, dated Apr. 19, 2017.
Radeck, Stephanie, "Office Action" for EP Office Action Application No. 13729770.0, dated Apr. 19, 2017.
Radeck, Stephanie, "Office Action" for EP Office Action Application No. 13730613.0, dated Apr. 19, 2017.
RU Office Action for Application No. 2015101291/02, dated Jun. 2, 2017.
RU Office Action for Application No. 2015102166/02, dated Jun. 2, 2017.
RU Office Action for Application No. 2015102168/02, dated Jun. 2, 2017.

(56) References Cited

OTHER PUBLICATIONS

Wang, Jinyong, "Notification of the First Office Action," Chinese Patent Application No. 201380022063.0, dated Feb. 1, 2016, 10 pages.
Wenjiang, Ding, "Science and Technology of Magnesium Alloys," Science Publishing House, Jan. 2007, pp. 323-324.
Xu, Yang, State Intellectual Property Office of the People's Republic of China Notification of the First Office Action, Application No. 201380022712.7, dated Feb. 29, 2017, 8 pages.
Xu, Yang, State Intellectual Property Office of the People's Republic of China Notification of the Second Office Action, Application No. 201380022712.7, dated Nov. 18, 2016, 10 pages.
Xu, Yang, State Intellectual Property Office of the People's Republic of China Notification of the Third Office Action, Application No. 201380022712.7, dated May 25, 2017, 10 pages.
Hanawalt, et al., Corrosion Studies of Magnesium and Its Alloys, Metals Technology, Sep. 1941, 273-299.
Li, Wen, et al., Preparation and in Vitro Degradation of the Composite Coating with High Adhesion Strength on Biodegradable Mg—Zn, Ca Alloy, Materials Characterization 62 (2011), 1158-1165.
Cha, Pil-Ryung, et al., Biodegradability Engineering of Biodegradable Mg Alloys: Tailoring the Electrochemical Properties and Microstructure of Constituent Phases, Scientific Reports 3:2367, 1-6, 2013.
Song, Yingwei, et al., The Role of Second Phases in the Corrosion Behavior of Mg—5Zn Alloy, Corrosion Science 60 (2012) 238-245.
Abidin, Nor Ishida Zainal, et al., Corrosion of High Purity Mg, Mg2Zn0.2Mn,ZE41 and AZ91 in Hank's Solution at 37° C., Corrosion Science 53 (2011) 3542-3556.
Bakhsheshi-Rad, H.R., et al., Relationship Between the Corrosion Behavior and the Thermal Characteristics and Microstructure of Mg—0.5Ca—xZn Alloys, Corrosion Science 64 (2012) 184-197.
Sugiura, Tsutomu, et al., A Comparative Evaluation of Osteosynthesis with Lag Screws, Miniplates, or Kirschner Wires for Mandibular Condylar Process Fractures, J. Oral Maxillofac Surg 59:1161-1168, 2001.
Manohar, P.A., et al., Five Decades of the Zenar Equation, ISIJ International, vol. 38 (1998), No. 9, pp. 913-924.
Wang, Bin, et al., Biocorrosion of Coated Mg—Zn—Ca Alloy under Constant Compressive Stress Close to that of Human Tibia, Materials Letters 70 (2012) 174-176.
Barnett, M.R., et al., Influence of Grain Size on the Compressive Deformation of Wrought Mg—3Al—1Zn, Acta Materiala 52 (2004) 5093-5103.
Du, Hui, et al., Effects of Zn on the Microstructure, Mechanical Property and Bio-Corrosion Property of Mg—3Ca Alloys for Biomedical Application, Materials Chemistry and Physics 125 (2011) 568-575.
Kirkland, Nicholas, et al., In Vitro Dissolution of Magnesium-Calcium Binary Alloys: Clarifying the Unique Role of Calcium Additions in Bioresorbable Magnesium Implant Alloys, Wiley Online Library, 2010, 91-100.
Zhang, Erlin, et al., Microstructure, Mechanical Properties and Bio-Corrosion Properties of Mg—Zn—Mn—Ca Alloy for Biomedical Application, Materials Science and Engineering A 497 (2008) 111-118.
Song, Guang Ling, et al., Understanding Magnesium Corrosion, A Framework for Improved Alloy Performance, Advanced Engineering Materials, 2003, 5, No. 12, 837-858.
Song, Guang Ling, et al., Corrosion Mechanisms of Magnesium Alloys, Advanced Engineering Materials, 1999, 1, No. 1, 11-33.
Abidin, Nor Ishida Zainal et a.., The In Vivo and In Vitro Corrosion of High-Purity Magnesium and Magnesium Alloys WZ21 and AZ91, Corrosion Science 75 (2013) 354-366.
Kirkland, N. T., et al., Assessing the Corrosion of Biodegradable Magnesium Implants: A Critical Review of Current Methodologies and Their Limitations, Acta Biomaterialia 8 (2012) 925-936.
Kirkland, Nicholas T., et al., Buffer-Regulated Biocorrrosion of Pure Magnesium, J. Mater Sci: Mater Med. (2012) 23: 283-291.

Hanzi, Anja C., et al., On the In Vitro and In Vivo Degradation Performance and Biological Response of New Biodegradable Mg—Y—Zn Alloys, Acta Biomateriala 6 (2010) 1824-1833.
Yamamoto, Akiko, et al., Effect of Inorganic Salts, Amino Acids and Proteins on the Degradation of Pure Magnesium in Vitro, Materials Science and Engineering C 29 (2009) 1559-1568.
Cao, Fuyong, et al., Corrosion of Ultra-High-Purity Mg in 3.5% NaCl Solution Saturated with Mg(OH)2, Corrosion Science 75 (2013) 78-99.
Kalb, H., et al., Impact of Microgalvanic Corrosion on the Degradation Morphology of WE43 and Pure Magnesium under Exposure to Simulated Body Fluid, Corrosion Science 57 (2012) 122-130.
Schinhammer, Michael, et al., On the Immersion Testing of Degradable Implant Materials in Simulated Body Fluid: Active pH Regulation Using CO2, Advanced Engineering Materials, 2013, 15, No. 6, 434-441.
Liu, Ming, et al., Calculated Phase Diagrams and the Corrosion of Die-Cast Mg—Al Alloys, Corrosion Science, 2009, 602-619.
Pilcher, Karin, et al., Immunological Response to Biodegradable Magnesium Implants, JOM, vol. 66, No. 4, 2014.
Kraus, Tanja, et al., Magnesium Alloys for Temporary Implants in Osteosynthesis: In Vivo Studies of their Degradation and Interaction with Bone, Acta Biomaterialia 8 (2012) 1230-1238.
Homma, T., et al., Effect of Zr Addition on the Mechanical Properties of as-Extruded Mg—Zn—Ca—Zr Alloys, Materials Science and Engineering A 527 (2010) 2356-2362.
Mendis, C.L., et al., Precipitation-Hardenable Mg—2.4Zn—0.1Ag—0.1Ca—0.16Zr (at.%) Wrought Magnesium Alloy, Acta Materialia 57 (2009) 749-760.
Koike, J., et al., The Activity of Non-Basal Slip Systems and Dynamic Recovery at Room Temperature in Fine-Grained AZ31B Magnesium Alloys, Acta Materialia 51 (2003) 2055-2065.
Hanzi, A.C., et al., Design Strategy for Microalloyed Ultra-Ductile Magnesium Alloys, Philosophical Magazine Letters, vol. 89, No. 6, Jun. 2009, 377-390.
Bamberger, M., et al., Trends in the Development of New Mg Alloys, Annu. Rev. Mater. Res. 2008, 38:505-33.
Farahany, Saeed, et al., In-Situ Thermal Analysis and Macroscopical Characterization of Mg—xCA and Mg—0.5Ca—KZn Alloy Systems, Thermochimica Acta 527 (2012) 180-189.
Zhang, Baoping, et al., Mechanical Properties, Degradation Performance and Cytotoxicity of Mg—Zn—Ca Biomedical Alloys with Different Compositions, Materials Science and Engineering C 31 (2011) 1667-1673.
Gunde, P., et al., High-Strength Magnesium Alloys for Degradable Implant Applications, Materials Science and Engineering,A 528 (2011) 1047-1054.
Stefanidou, M. et al., Zinc: A Multipurpose Trace Element, Arch Toxicol (2006) 80: 1-9.
Tapiero, Haim, et al., Trace Elements in Human Physiology and Pathology: Zinc and Metallothioneins, Biomedicine & Pharmacotherapy 57 (2003) 399-411.
Hanzi, A.C., et al., Design Considerations for Achieving Simultaneously High-Strength and Highly Ductile Magnesium Alloys, Philosophical Magazine Letters 2012, 1-11.
Zberg, Bruno, et al, MgZnCa Glasses Without Clinically Observable Hydrogen Evolution for Biodegradable Implants, Nature Materials, vol. 8, Nov. 2009, 887-891.
Staiger, Mark P., et al., Magnesium and its Alloys as Orthopedic Biomaterials: A Review, Biomaterials 27 (2006) 1728-1734.
Witte, Frank, et al., Degradable Biomaterials Based on Magnesium Corrosions, Current Opinion in Solid State and Materials Science (2009).
Zhang, Shaoxiang, et al., Research on an Mg—Zn Alloy as Degradable Biomaterial, Acta Biomaterialia 6 (2010) 626-640.
Song, Guangling, Control of Biodegradation of Biocompatable Magnesium Alloys, Corrosion Science 49 (2007) 1696-1701.
Hofstetter, J., et al., High-Strength Low-Alloy (HSLA) Mg—Zn—Ca Alloys with Excellent Biodegradation Performance, JOM, vol. 66, No. 4, 2014.
Mendis, C.L., et al., An Enhanced Age Hardening Response in Mg—Sn Based Alloys Containing Zn, Materials Science and Engineering A 435-436 (2006) 163-171.

(56) References Cited

OTHER PUBLICATIONS

Sudholz, A.D., et al., Corrosion Behaviour of Mg-Alloy AZ91E with Atypical Alloying Additions, Journal of Alloys and Compounds 471 (2009) 109-115.
Chia, T.L., et al., The Effect of Alloy Composition on the Microstructure and Tensile Properties of Binary Mg-rare Earth Alloys, Intermetallics 17 (2009) 481-490.
Birbilis, N., et al., On the Corrosion of Binary Magnesium-Rare Earth Alloys, Corrosion Science 51 (2009) 683-689.
Birbilis, N., et al., A Combined Neural Network and Mechanistic Approach for the Prediction of Corrosion Rate and Yield Strength of Magnesium-Rare Earth Alloys, Corrosion Science 53 (2011) 168-176.
A.D. Sudholz, et al., Electrochemical Properties of Intermetallic Phases and Common Impurity Elements in Magnesium Alloys, Electrochemical and Solid-State Letters, 14 (2) C5-C7 (2011).
Shaw, Barbara, Corrosion Resistance of Magnesium Alloys, ASM Handbook, vol. 13A, 2003,692-696.
Bakhsheshi-Rad, et al., Characterization and Corrosion Behavior of Biodegradable Mg—Ca and Mg—Ca—Zn Implant Alloys, Appl. Mech. Mater, Jan. 2012, 121-126, 568-572 (Abstract Only).
Sun, Yu, et al., Preparation and Characterization of a New Biomedical Mg—Zn—Ca Alloy, Materials and Design, vol. 34, pp. 56-64, Feb. 2012 (Abstract Only).
Koike, Junichi, Dislocation Plasticity and Complementary Deformation Mechanisms in Polycrystalline Mg Alloys, Mater. Sci. Forum, Mar. 2004, 4999-452, 665-668 (Abstract Only).
Wilson, D.V., et al., Effects of Preferred Orientation on the Grain Size Dependence of Yield Strength in Metals, Philos. Mag., Jun. 1963, 1543-1551 (Abstract Only).
L'Ecuyer, J.D., et al., Precipitation Interactions with Dynamic Recrystallization of HSLS Steel, Acta Metallurigica, Apr. 1989, 37, 4, 1023-1031 (Abstract Only).
International Search Report for PCT/US2014/023047, dated Jan. 31, 2014.
International Search Report for PCT/US2013/057294, dated Jun. 17, 2014.
Xu, Bingshe, et al., 1200 Questions on Nonferrous Metallurgy; 747, How to Prepare Highly Pure Magnesium, Jan. 1, 2008.
ASTM International, Standard Specification for Magnesium-Alloy Die Castings, 1998.
European Committee for Standardization, Magnesium and Magnesium Alloys, 1998.

* cited by examiner

MAGNESIUM-ZINC-CALCIUM ALLOY, METHOD FOR PRODUCTION THEREOF, AND USE THEREOF

PRIORITY CLAIM

This application is a U.S. National Phase under 35 U.S.C. § 371 of International Application No. PCT/EP2013/063111, filed Jun. 24, 2013, which claims priority to U.S. Provisional Application No. 61/664,274, filed Jun. 26, 2012.

FIELD OF THE INVENTION

A field of the invention relates to a magnesium alloy and to a method for the production thereof and to the use thereof. Magnesium alloys of the invention are applicable to implants, including cardiovascular, osteosynthesis, and tissue implants. Example applications include stents, valves, closure devices, occluders, clips, coils, staples, implantable regional drug delivery devices, implantable electrostimulators (like pacemakers and defibrillators), implantable monitoring devices, implantable electrodes, systems for fastening and temporarily fixing tissue implants and tissue transplantations. Additional example applications include implantable plates, pins, rods, wires, screws, clips, nails, and staples.

BACKGROUND

Magnesium properties are defined by the type and quantity of the alloying elements and impurities as well as the production conditions. Some effects of the alloying elements and impurities on the properties of the magnesium alloys have been long known to artisans. However, the properties of binary or ternary magnesium alloys for the use thereof as implant materials remains complex to determine.

The alloying element used most frequently for magnesium is aluminum, resulting in increased tensile strength due to solid solution and precipitation hardening and fine grain formation, but also in microporosity. Moreover, in the melt aluminum shifts the iron precipitation boundary toward drastically lower iron contents at which the iron particles precipitate or form intermetallic particles together with other elements.

Calcium exhibits a pronounced grain refining effect and worsens the castability and corrosion resistance.

Undesirable accompanying elements in magnesium alloys include iron, nickel, cobalt and copper, which cause a considerable increase in the corrosion tendency due to the electropositive nature thereof.

Manganese can be found in all magnesium casting alloys and binds iron in the form of AlMnFe precipitations, whereby the formation of local elements is reduced. On the other hand, manganese is not able to bind all the iron, and therefore a remainder of iron and a remainder of manganese always remain in the melt.

Silicon lowers the castability and viscosity, and as the content of Si rises, a worsened corrosion behavior is to be expected. Iron, manganese and silicon have a very high tendency to form an intermetallic phase. The electrochemical potential of this phase is very high and can thus act as a cathode controlling the corrosion of the alloy matrix.

As a result of solid solution hardening, zinc improves the mechanical properties and results in grain refining, however it also leads to microporosity with a tendency toward hot cracking starting at a content of 1.5 to 2% by weight in binary Mg—Zn and ternary Mg—Al—Zn alloys.

Alloying additions made of zirconium increase the tensile strength without lowering the expansion and lead to grain refining, but also to a strong impairment of dynamic recrystallization, which is manifested in an increase of the recrystallization temperature and therefore requires high energy expenditure. Moreover, zirconium cannot be added to melts containing aluminum and silicon because the grain refining effect is lost.

Rare earths such as Lu, Er, Ho, Th, Sc and In all exhibit a similar chemical behavior and form eutectic systems with partial solubility on the magnesium-rich side of the binary phase diagrams such that precipitation hardening is possible.

The addition of further alloying elements, in conjunction with the impurities, is known to cause the formation of different intermetallic phases in binary magnesium alloys. For example, the intermetallic phase $Mg_{17}Al_{12}$ forming at the grain boundaries is brittle and limits the ductility. As compared to the magnesium matrix, this intermetallic phase is more noble and able to form local elements, whereby the corrosion behavior worsens.

In addition to these influencing factors, the properties of the magnesium alloys also depend on the metallurgical production conditions. Conventional casting methods automatically introduce impurities when adding, by alloying, the alloying elements. The prior art (U.S. Pat. No. 5,055,254 A) defines tolerance limits for impurities in magnesium casting alloys, which, for example for a magnesium-aluminum-zinc alloy containing approximately 8 to 9.5% Al and 0.45 to 0.9% Zn, mentions tolerance limits of 0.0015 to 0.0024% Fe, 0.0010% Ni, 0.0010 to 0.0024% Cu and no less than 0.15 to 0.5% Mn.

Tolerance limits for impurities in magnesium and the alloys therefore are stated in a variety of technical literature as follows:

| Alloy | Production | State | Fe | Fe/Mn | Ni | Cu |
|---|---|---|---|---|---|---|
| Pure Mg | no information | | 0.017 | | 0.005 | 0.01 |
| AZ 91 | Die casting | F | | 0.032 | 0.005 | 0.040 |
| | High-pressure die casting | | | 0.032 | 0.005 | 0.040 |
| | Low-pressure die casting | | | 0.032 | 0.001 | 0.040 |
| | | T4 | | 0.035 | 0.001 | 0.010 |
| | | T6 | | 0.046 | 0.001 | 0.040 |
| | Gravity die casting | F | | 0.032 | 0.001 | 0.040 |
| AM60 | Die casting | F | | 0.021 | 0.003 | 0.010 |
| AM50 | Die casting | F | | 0.015 | 0.003 | 0.010 |
| AS41 | Die casting | F | | 0.010 | 0.004 | 0.020 |
| AE42 | Die casting | F | | 0.020 | 0.020 | 0.100 |

It has been found that these tolerance definitions are not sufficient to reliably exclude the formation of corrosion-promoting intermetallic phases, which in terms of electrochemistry have a more noble potential than the magnesium matrix.

Biodegradable implants require a load-bearing function and consequently strength, together with sufficient expandability, during the physiologically necessary support periods thereof. However, especially in this respect, the known magnesium materials fall far short of the strength properties provided by permanent implants such as titanium, CoCr alloys and titanium alloys. The ultimate tensile strength $R_m$ for implants is approximately 500 MPa to >1000 MPa, while that of magnesium materials is <275 MPa so far, and in most cases <250 MPa.

Another drawback of many technical magnesium materials is that the difference thereof between ultimate tensile strength $R_m$ and proof stress $R_p$ is small. In the case of implants that allow plastic deformation, such as cardiovascular stents, this means that no further resistance exists against deformation after initial deformation of the material, and the regions that have already been deformed are deformed further without any load increase This can lead to overstretching of parts of the component and fracture may occur.

Many magnesium materials, such as the alloys of the AZ group, for example, additionally exhibit a clearly pronounced mechanical asymmetry, which is manifested in the difference in the mechanical properties, especially the proof stress $R_p$ with tension load and compression load. Such asymmetries are created, for example, during forming processes such as extrusion, rolling and drawing, which are used to produce suitable semi-finished products. A difference between the proof stress $R_p$ during tension and the proof stress $R_p$ during compression that is too large may result in inhomogeneous deformation of a component, such as a cardiovascular stent, which later undergoes multiaxial deformation, and may cause cracking and fracture.

Because of the low number of crystallographic slip systems, magnesium alloys can generally also form textures during forming processes such as extrusion, rolling and drawing used to produce suitable semifinished products by orienting the grains during the forming process. Specifically, the semifinished product has different properties in different directions in space. For example, high deformability or elongation at fracture occurs in one direction in space after forming, and reduced deformability or elongation at fracture occurs in another direction in space. The formation of such textures should likewise be avoided, because a stent is subjected to high plastic deformation, and reduced elongation at fracture increases the risk of failure of the implant. One method for substantially avoiding such textures during forming is to adjust as fine a grain as possible prior to forming. Because of the hexagonal lattice structure of magnesium materials, the ability of these materials to deform at room temperature is low, which is characterized by slip in the base plane. If the material additionally has a coarse microstructure, i.e., a coarse grain, so-called twinning is forcibly produced upon further deformation, at which shear strain occurs, which transforms a crystal region into a position that is mirror symmetrical to the starting position. The resulting twin grain boundaries constitute weak points in the material, where incipient cracking starts, especially with plastic deformation, which ultimately leads to the destruction of the component.

If the grain of the implant materials is sufficiently fine, the risk of such implant failure is drastically reduced. Implant materials should therefore have as fine a grain as possible so as to prevent such undesirable shear strain.

All available magnesium materials for implants are subject to high corrosion in physiological media. Attempts have been made in the prior art to curb the corrosion tendency by providing the implants with a corrosion-inhibiting coating, for example made of polymeric materials (EP 2 085 100 A2, EP 2 384 725 A1), an aqueous or alcoholic conversion solution (DE 10 2006 060 501 A1) or an oxide (DE 10 2010 027 532 A1, EP 0 295 397 A1).

The use of polymeric passivation layers is controversial, because virtually all appropriate polymers also cause strong inflammations in the tissue at times. Thin structures without such protective measures do not provide the required support periods. The corrosion on thin-walled traumatological implants is often times accompanied by an excessively fast loss of tensile strength, which poses an additional burden by forming excessive amounts of hydrogen per unit of time. The consequences are undesirable gas inclusions in the bones and tissue.

In the case of traumatological implants having larger cross-sections, there is a need to be able to deliberately control the hydrogen problem and the corrosion rate of the implant by way of the structure thereof.

Specifically with biodegradable implants, there is a desire for maximum biocompatibility of the elements, because all the chemical elements that are contained are absorbed by the body after decomposition. In any case, highly toxic elements such as Be, Cd, Pb, Cr and the like should be avoided.

Degradable magnesium alloys are especially suitable for implementing implants which have been employed in a wide variety of forms in modern medical technology. Implants are used, for example, to support vessels, hollow organs and vein systems (endovascular implants, such as stents), for fastening and temporarily fixing tissue implants and tissue transplantations, but also for orthopedic purposes, such as nails, plates or screws. A particularly frequently used form of an implant is the stent.

The implantation of stents has become established as one of the most effective therapeutic measures for the treatment of vascular diseases. Stents have the purpose of assuming a supporting function in hollow organs of a patient. For this purpose, stents featuring conventional designs have a filigree supporting structure comprising metal struts, which is initially present in compressed form for introduction into the body and is expanded at the site of the application. One of the main application areas of such stents is to permanently or temporarily widen and hold open vascular constrictions, particularly constrictions (stenosis) of coronary blood vessels. In addition, aneurysm stents are known, which are used primarily to seal the aneurysm. The support function is additionally provided.

A stent has a base body made of an implant material. An implant material is a non-living material, which is employed for applications in medicine and interacts with biological systems. A basic prerequisite for the use of a material as an implant material, which is in contact with the body environment when used as intended, is the body friendliness thereof (biocompatibility). For the purpose of the present application, biocompatibility shall be understood to mean the ability of a material to induce an appropriate tissue reaction in a specific application. This includes an adaptation of the chemical, physical, biological, and morphological surface properties of an implant to the recipient's tissue with the aim of a clinically desired interaction. The biocompatibility of the implant material is also dependent on the temporal process of the reaction of the biosystem in which it is implanted. For example, irritations and inflammations occur in a relatively short time, which can lead to tissue changes. Depending on the properties of the implant material, biological systems thus react in different ways. According to the reaction of the biosystem, the implant materials can be divided into bioactive, bioinert and degradable or resorbable materials.

Conventional implant materials include polymers, metallic materials, and ceramic materials (as coatings, for example). Biocompatible metals and metal alloys for permanent implants include, for example, stainless steels (such as 316L), cobalt-based alloys (such as CoCrMo cast alloys, CoCrMo forge alloys, CoCrWNi forge alloys and CoCrNiMo forge alloys), pure titanium and titanium alloys (such as cp titanium, TiAl6V4 or TiAl6Nb7) and gold alloys. In the field of biocorrodible stents, the use of magnesium or pure iron as well as biocorrodible base alloys of the elements magnesium, iron, zinc, molybdenum, and tungsten are known.

The use of biocorrodible magnesium alloys for temporary implants having filigree structures is made difficult in particular in that the degradation of the implant progresses very quickly in vivo. Alloy composition and coatings are approaches to slow the degradation of the implant material While the existing approaches have shown promise, none of them has so far led to a commercially available product to the knowledge of the inventors. Regardless of the efforts made so far, there remains a continuing need for solutions that make it possible to at least temporarily reduce the corrosion of magnesium alloys in vivo, while optimizing the mechanical properties thereof at the same time.

SUMMARY OF THE INVENTION

Preferred embodiments of the invention provide a biodegradable magnesium alloy, and a method for the production thereof and implants, which allow the magnesium matrix of the implant to remain in an electrochemically stable state over the required support period with fine grain and high corrosion resistance without protective layers, and to utilize the formation of intermetallic phases, which electrochemically are more noble than the magnesium matrix, while also improving the mechanical properties, such as increasing the tensile strength and proof stress, as well as reducing the mechanical asymmetry so as to adjust the degradation rate of the implants.

A preferred magnesium alloy includes 3 to 7% by weight Zn, 0.001 to 0.5% by weight Ca, the remainder being magnesium containing total impurities, which promote electrochemical potential differences and/or the formation of intermetallic phases, in a total amount of no more than 0.0048% by weight, preferably no more than 0.0045% by weight and still more preferably no more than 0.0036% by weight, wherein the total impurity contains:

individual impurities selected from the group of Fe, Si, Mn, Co, Ni, Cu, Al, Zr and P in an amount of not more than 0.0038% of weight; and alloying elements selected from the group of the rare earths having the ordinal numbers 21, 39, 57 to 71 and 89 to 103 in an amount of no more than 0.001% by weight.

A preferred method for producing a magnesium alloy having improved mechanical and electrochemical properties includes generating a high-purity magnesium by vacuum distillation. A billet of the alloy is generated by synthesis of the high-purity magnesium according with high-purity Zn and Ca in a composition of 3 to 7% by weight Zn, 0.001 to 0.5% by weight Ca, the remainder being magnesium containing total impurities, which promote electrochemical potential differences and/or the formation of intermetallic phases, in an amount of no more than 0.0048 by weight wherein the total impurity contains individual impurities selected from the group of Fe, Si, Mn, Co, Ni, Cu, Al, Zr and P in an amount of not more than 0.0038% of weight; with the alloying elements are selected from the group of the rare earths having the ordinal numbers 21, 39, 57 to 71 and 89 to 103 in a total amount of no more than 0.001% by weight. The alloy is homogenized by annealing at a temperature between 350° C. and 450° C. with a holding period of 4 to 40 hours. The homogenized alloy is formed in the temperature range between 250° C. and 350° C. The formed alloy is optionally heat treated in the temperature range between 100° C. and 300° C. with a holding period of 1 minute to 3 hours.

DETAILED DESCRIPTION OF THE PREFERRED EMBODIMENTS

The magnesium alloy according to the invention has extraordinarily high corrosion resistance, which is achieved by drastically reducing the content of individual impurities and the combinations thereof in the magnesium matrix, and by also adding precipitation and solid solution hardenable elements, which are present in completely solid solution. The microstructure that is obtained has no electrochemical potential differences between the individual matrix phases after the forming and heat treatment processes, and therefore these differences cannot expedite the corrosion in physiological media. The solution according to the invention is based on the realization that the corrosion resistance and deformability of the magnesium matrix of the implant must be assured over the support period such that the implant is able to absorb multiaxial permanent load without fracture or cracking, and to also utilize the magnesium matrix as a means for the decomposition triggered by the physiological liquids.

The applicant surprisingly found that the alloy matrix, having a content of 3 to 5% by weight Zn and 0.2 to 0.4% by weight Ca, has a more noble electrochemical potential than the intermetallic phase $Ca_2Mg_6Zn_3$, while the MgZn phase, which can be precipitated by heat treatment, is considerably more noble as compared to the alloy matrix, whereby the MgZn phase can be precipitated from the lattice of the alloy matrix by means of targeted heat treatment and can act as cathodes for the alloy matrix. This provides the option of deliberately influencing the degradation rate of the alloy matrix.

Another surprising result is that, despite freedom of Zr, or Zr contents that are considerably lower than those stated in the prior art, a grain refining effect can be achieved which is attributed to the intermetallic phase $Ca_2Mg_6Zn_3$, which blocks the movements of the grain boundaries, limits the grain size during recrystallization and thus prevents undesirable grain growth, while also increasing the proof stress and tensile strength values.

Within the aforementioned mechanical properties, a Zr content of <0.0003% by weight, and preferably <0.0001% by weight, is advantageous for the magnesium alloy according to the invention.

The previously known tolerance limits for the individual impurities within the total impurity do not take into account that wrought magnesium alloys often times are subjected to a thermomechanical treatment, and more particularly to an extended annealing process, which creates the near-equilibrium structures. The metallic elements bond by way of diffusion and form what are known as intermetallic phases, which have a different electrochemical potential, notably a considerably higher potential, than the magnesium matrix, and therefore these intermetallic phases act as cathodes and can trigger galvanic corrosion processes.

The applicant found that a formation of such intermetallic phases can be reliably prevent when complying with the following tolerance limits of the individual impurities within the total impurity:

Fe, Si, Mn, Co, Ni, Cu each with <0.0005% by weight; Zr, Al each with <0.0003% by weight; and P<0.0002% by weight.

It is noted that in this embodiment the total impurity additionally contains individual impurities selected from the group of rare earths having the ordinal numbers 21, 57 to 71 and 89 to 103 in total <0.001% by weight, preferably no more than 0.0005% by weight and still more preferably no more than 0.0003% by weight.

Preferably, the corrosion-staple alloy matrix contains total impurities in a total amount of no more than 0.0036% by weight, containing individual impurities selected from the group of Fe, Si, Mn, Co, Ni, Al, Zr, and P of in total no more than 0.0026% by weight, wherein the total amount can be achieved when complying with the following tolerance limits of individual impurities in % by weight:
Fe, Si, Mn each with <0.0005; Co, Ni, Cu each with <0.0002; Zr, <0.0003; and P, Al each with <0.0001.

Additionally the total impurities contain the preferred amount of rare earths having the ordinal numbers 21, 57 to 71 and 89 to 103 in total <0.001.

In particular preferred the corrosion-staple alloy matrix contains total impurities in a total amount of no more than 0.00215% by weight, containing individual impurities selected from the group of Fe, Si, Mn, Co, Ni, Al, Zr, and P of in total no more than 0.00115% by weight, wherein the total amount can be achieved when complying with the following tolerance limits of individual impurities in % by weight:
Fe, Si, Mn each with <0.0002; Co, Ni, Cu, Zr, P each with <0.0001; and Al<0.00005.

Additionally the total impurities contain the preferred amount of rare earths having the ordinal numbers 21, 57 to 71 and 89 to 103 in total <0.001.

When the individual impurities are combined, the formation of intermetallic phases, which are more noble than the alloy matrix, is suppressed if the sum of individual impurities consisting of Fe, Si, Mn, Co, Ni, Cu and Al is no more than 0.0033% by weight, preferably no more than 0.0022% by weight, still more preferably no more than 0.00095% by weight, the content of Al is no more than 0.0003% by weight, preferably no more than 0.0001% by weight, particularly preferably no more than 0.00005% by weight and the content of Zr is preferably no more than 0.0003% by weight, preferably no more than 0.0001% by weight.

There are different mechanisms of action by which the aforementioned individual impurities impair the corrosion resistance of the material.

If small Fe particles form in the alloy because of a high Fe content, these particles will act as cathodes for a corrosive attack; the same applies to Ni and Cu.

Moreover, especially Fe and Ni with Zr, but also Fe, Ni and Cu with Zr, can precipitate as intermetallic particles in the melt; these will also act as very effective cathodes for corrosion of the matrix.

Intermetallic particles having a very high potential difference as compared to the matrix and a very high formation tendency include the phases of Fe and Si and Fe, Mn and Si, which is why contaminations containing these elements must be minimized.

The content of P should be minimized to the extent possible, because Mg phosphides form even when minute amounts of P are present and dramatically impair the mechanical properties of the structure.

Such low concentrations thus ensure that the magnesium matrix no longer contains any intermetallic phases, which have a more positive electrochemical potential as compared to the matrix.

In the preferred magnesium alloy according to the invention, the sum of the contents of elements of the rare earths and scandium (ordinal numbers 21, 57 to 71 and 89 to 103) is less than 0.001% by weight, preferably less than 0.0005% by weight and still more preferably less than 0.0003.

These additions make it possible to increase the tensile strength of the magnesium matrix and raise the electrochemical potential of the matrix, whereby a corrosion-reducing action, notably with respect to physiological media, develops. The precipitations preferably have a size of no more than 5 µm, and preferably of no more than 1 µm, and are located on the grain boundaries and in the grain interior, whereby the movement of grain boundaries during thermal treatment as well as dislocations during deformation are impaired and the strength of the magnesium alloy is increased.

The magnesium alloy according to the invention achieves a tensile strength of >275 MPa, and preferably >300 MPa, a yield point of >200 MPa, and preferably >225 MPa, and a yield ratio of <0.8, and preferably <075, wherein the difference between the tensile strength and yield point is >50 MPa, and preferably >100 MPa, and the mechanical asymmetry is <1.25.

These significantly improved mechanical properties of the novel magnesium alloys assure that the implants, for example cardiovascular stents, are able to withstand the multiaxial permanent load in the implanted state over the entire support period, despite onsetting degradation of the magnesium matrix due to corrosion.

So as to minimize the mechanical asymmetry, it is preferable for the magnesium alloy to have a particularly fine microstructure having a grain size of no more than 5 µm.

A preferred method for producing a magnesium alloy having improved mechanical and electrochemical properties is provided. The method includes the following steps:
a) generating a high-purity magnesium by way of vacuum distillation;
b) generating a billet of the alloy by synthesis of the magnesium according to step a) with high-purity Zn and Ca in a composition of 3 to 7% by weight Zn, 0.001 to 0.5% by weight Ca, the remainder being magnesium containing total impurities, which promote electrochemical potential differences and/or the formation of intermetallic phases, in a amount of no more than 0.0048 by weight, preferably no more than 0.0045% by weight and still more preferably no more than 0.0036% by weight, wherein the total impurity contains individual impurities selected from the group of Fe, Si, Mn, Co, Ni, Cu, Al, Zr and P in an amount of not more than 0.0038% of weight; and wherein the alloying elements are selected from the group of the rare earths having the ordinal numbers 21, 39, 57 to 71 and 89 to 103 in a total amount of no more than 0.001% by weight;
c) homogenizing the alloy by annealing at a temperature between 350° C. and 450° C. with a holding period of 4 to 40 hours;
c) at least single forming of the homogenized alloy in the temperature range between 250° C. and 350° C.; and
d) optionally heat treating the formed alloy in the temperature range between 100° C. and 300° C. with a holding period of 1 minute to 3 hours.

A content of preferably 3 to 5% by weight Zn and a content of 0.2 to 0.4% by weight Ca assure that volume contents of up to 2% of the intermetallic phase and the precipitable MgZn phase, respectively, are created in the matrix lattice. The electrochemical potentials of the two phases differ considerably, the MgZn phase being more noble than the matrix and the $Ca_2Mg_6Zn_3$ phase being less noble than the matrix. By means of the heat treatment, the MgZn phase can be prompted to precipitate to the desired degree in a regime preselected by the temperature and holding period, whereby the degradation rate of the alloy matrix can be adjusted.

In addition to the corrosion-inhibiting action, the intermetallic $Ca_2Mg_6Zn_3$ phase also has the surprising effect of grain refining created by the forming process, which results in a considerable increase in tensile strength and proof stress. This allows Zr to be dispensed with as an alloying element and the temperatures for the recrystallization to be lowered.

Vacuum distillation is preferably used to produce a starting material for a high-purity magnesium-zinc-calcium alloy having the required threshold values.

The sum of impurities and the content of addition elements triggering the precipitation and solid solution hardening and raising the matrix potential can be selectively adjusted and in % by weight are:

a) for the individual impurities:
Fe, Si, Mn, Co, Ni, Cu each with <0.0005% by weight;
Al, Zr each with <0.0003% by weight;
and P<0.0002% by weight.

It is noted that in this embodiment the total impurity additionally contains individual impurities selected from the group of rare earths having the ordinal numbers 21, 57 to 71 and 89 to 103 in total <0.001% by weight.

aa) for the individual impurities in a preferred amount of impurities of no more than 0.0026% by weight:
Fe, Si, Mn each with <0.0005;
Co, Ni, Cu each with <0.0002;
Zr, <0.0003; and
Al, P each with <0.0001.

In this preferred embodiment the amount of total impurities which is the sum of the individual impurities and the impurities selected from the group of rare earths having the ordinal numbers 21, 57 to 71 and 89 to 103 is in total <0.0036% by weight.

ab) for the individual impurities in a particularly preferred amount of impurities of no more than 0.00115% by weight:
Fe, Si, Mn each with <0.0002;
Co, Ni, Cu, Zr, P each with <0.0001; and
Al<0.0001.

In this preferred embodiment the amount of total impurities which is the sum of the individual impurities and the impurities selected from the group of rare earths having the ordinal numbers 21, 57 to 71 and 89 to 103 is in total <0.00215% by weight.

b) for the combination of individual impurities in total:
Fe, Si, Mn, Co, Ni, Cu and Al no more than 0.0033% by weight, preferably no more than 0.0022% by weight, still more preferably 0.00095% by weight, the content of Al no more than 0.0003 preferably no more than 0.0001% by weight, particularly preferably no more than 0.00005% by weight, and the content of Zr is no more than 0.0003% by weight, preferably no more than 0.0001% by weight;

c) for the addition elements which are also contained in the total impurities:
rare earths in a total amount of no more than 0.001% by weight, preferably no more than 0.0005% by weight.

It is particularly advantageous that the method according to the invention only requires a small number of forming steps. Extrusion, equal channel angular extrusion and/or multiple forging can thus preferably be employed, which assure that a substantially homogeneous fine grain of <15 μm is achieved.

Because of the heat treatment, MgZn precipitations having a grain size of 1 nm to 50 nm in a fine-grained structure having a grain size of preferably <7.5 μm dispersely distributed at the grain boundaries and in the interior of the grains, whereby the tensile strength of the alloy reaches values which at >275 MPa, and preferably >300 MPa, are considerably higher than the prior art.

The invention also relates to the use of the magnesium alloy produced according to the invention, which has the above described advantageous composition and structure, in medical technology, notably for the production of implants, for example endovascular implants such as stents, for fastening and temporarily fixing tissue implants and tissue transplantations, orthopedic and dental implants, and neuroimplants.

Preferred implants in the sense of this patent application are in the Cardiovascular field, osteosynthesis field or other areas.

Cardiovascular field in the sense of this application includes
the field of diagnostic, prevention and treatment of all diseases of the cardiovascular system, i.e. heart and blood vessel system,
by mean of active and non-active implants used to support vessels, and vein systems
including coronary, cerebral and peripheral vascular implants like stents, valves, closure devices, occluders, clips, coils, staples, implantable regional drug delivery devices,
implantable electrostimulators (like pacemakers and defibrillators), implantable monitoring devices, implantable electrodes,
system for fastening and temporarily fixing tissue implants and tissue transplantations
field also includes any type of stent as mechanical fix or temporary scaffold to support hollow organs including bones, intervertebral disks Osteosynthesis in the sense of this application includes the field of treatment of fractured bones for internal fixation and stabilization by mechanical devices such as metal plates, pins, rods, wires, screws, clips, nails, staples excluding stent technology Examples of areas out of the osteosynthesis field or the cardiovascular field are:
Devices for the treatment of diseases of the sinews, joints, muscles, cartilages,
oral (including dental) and maxillo facial implants (excl. osteosynthesis means),
esthetic implants,
supporting tools out of the body,
tissue engineering,
soft tissue implants,
devices for wound care,
suture material and clamps,
neurosurgery
local drug delivery (excl. cardiovascular, i.e. lever)
renal applications

EXAMPLE

A magnesium alloy is generated which is composed of 5% by weight Zn and 0.15% by weight Ca, the remainder being Mg, and contains the following individual impurities in % by weight:

Fe: <0.0005; Si: <0.0005; Mn: <0.0005; Co: <0.0002; Ni: <0.0001; Cu<0.0002, wherein the sum of individual impurities consisting of Fe, Si, Mn, Co, Ni, Cu and Al should be no more than 0.0015% by weight, the content of Al<0.001% by weight and that of Zr<0.0003% by weight, and the content of rare earths having the ordinal numbers 21, 39, 57 to 71 and 89 to 103 in total should be less than 0.001% by weight, which leads to an alloy with total impurities of in total no more than 0.0035% by weight.

This alloy, produced using magnesium vacuum distillation, is subjected to homogenizing annealing at a temperature of 350° C. for a duration of 12 hours, and subsequently to multiple extrusion processes at a temperature of 300° C., so as to produce a precision tube for a cardiovascular stent.

The subsequent heat treatment was carried out at a temperature of 250° C. with a holding period of 0.1 hour. The grain size was <7.5 μm.

The magnesium alloy reached a tensile strength of 310 to 320 MPa and proof stress of <250 MPa [sic]. The yield ratio was 0.7 and the mechanical asymmetry was 1.2.

In artificial body fluid, the $Ca_2Mg_6Zn_3$ phase degraded more quickly than the matrix and is therefore less noble than the matrix. This means that these intermetallic particles cannot act as cathodes for the alloy matrix. The MgZn phase expedited the degradation in artificial body fluid and was therefore more noble electrochemically than the alloy matrix, whereby it is able to induce corrosion.

Because of the subsequent heat treatment, it is thus possible to precipitate the MgZn phase from the alloy matrix, rendering the alloy matrix less noble.

The subsequent degradation rate under physiological usage conditions can thus be adjusted by means of the heat treatment.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A biodegradable implant formed from a magnesium alloy having improved mechanical and electrochemical properties, the magnesium alloy comprising: 3 to 7% by weight Zn, 0.001 to 0.5% by weight Ca, the remainder being high-purity vacuum distilled magnesium, the magnesium alloy containing total impurities, which promote electrochemical potential differences and/or the formation of intermetallic phases, in a total amount of no more than 0.0048% by weight wherein the total impurity contains:
  individual impurities selected from the group of Fe, Si, Mn, Co, Ni, Cu, Al, Zr and P in an amount of not more than 0.0038% of weight; and
  alloying elements selected from the group of the rare earths having the ordinal numbers 21, 39, 57 to 71 and 89 to 103 in an amount of no more than 0.001% by weight;
  wherein the biodegradable implant has a tensile strength of >275 MPa, a yield point of >200 MPa, and a yield ratio of <0.8, and wherein the difference between the tensile strength and yield point is >50 MPa;
  wherein the magnesium alloy contains an intermetallic $Ca_2Mg_6Zn_3$ phase; and
  wherein the implant has improved corrosion resistance.

2. The implant according to claim 1, wherein the total impurities have an amount in total of no more than 0.0045% by weight.

3. The implant according to claim 1, wherein the content of Zn is 3 to 5% by weight and that of Ca is at least 0.2 to 0.4% by weight, wherein the alloy contains an intermetallic $Ca_2Mg_6Zn_3$ phase in a volume content of greater than 0 to 2%.

4. The implant according to claim 1, total impurities amount to the following in % by weight: Fe<0.0005; Si<0.0005; Mn<0.0005; Co<0.0005; Ni<0.0005; Cu<0.0005; Al<0.0003; Zr<0.0003; P<0.0002.

5. The implant according to claim 1, wherein the impurity elements Fe, Si, Mn, Co, Ni, Cu and Al total no more than 0.0033% by weight, the content of Al is no more than 0.0003% by weight, and the content of Zr is no more than 0.0001% by weight.

6. The implant according to claim 1, wherein individual elements from the group of the rare earths together total no more than 0.001% by weight.

7. The implant according to claim 1, wherein the alloy has a fine-grained microstructure having a grain size of less than 7.5 μm, without considerable electrochemical potential differences between the individual matrix phases.

8. The implant according claim 1, wherein the alloy contains an intermetallic $Ca_2Mg_6Zn_3$ phase and a precipitable MgZn phase, and the intermetallic $Ca_2Mg_6Zn_3$ phase is at least equally as noble as, or less noble, and the precipitable MgZn phase is more noble, than the matrix phases.

9. The implant according to claim 1, wherein precipitations have a size of <5 μm and are dispersely distributed at the grain boundaries or in the grain interior.

10. The implant according to claim 1, wherein the mechanical asymmetry is <1.25.

11. The implant of claim 1, comprising one of stents, implants for fastening and temporarily fixing tissue implants and tissue transplantations, orthopedic and dental implants, and neuroimplants.

12. The implant according to claim 1, wherein the total impurities have an amount in total of no more than 0.0036% by weight.

13. The implant according to claim 1, wherein the impurity elements Fe, Si, Mn, Co, Ni, Cu and Al total no more than 0.0022% by weight, and the content of Al is no more than 0.0001% by weight.

14. The implant according to claim 13, wherein the impurity elements Fe, Si, Mn, Co, Ni, Cu and Al total no more than 0.00095% by weight, and the content of Al is no more than 0.00005% by weight.

15. The implant according to claim 1, wherein individual elements from the group of the rare earths together total no more than 0.0005% by weight.

16. The implant according to claim 1, wherein individual elements from the group of the rare earths together total no more than 0.0003% by weight.

17. The implant according to claim 1, wherein precipitations have a size of <1 μm and are dispersely distributed at the grain boundaries or in the grain interior.

18. The implant according to claim 1, having a tensile strength of >300 MPa, a yield point of >225 MPa, and a yield ratio of <0.75, wherein the difference between the tensile strength and yield point is >100 MPa, and the mechanical asymmetry is <1.25.

19. The implant according to claim 1, wherein the magnesium alloy forms a body of a cardiovascular implant.

20. The implant according to claim 1, wherein magnesium alloy comprises 5 to 7% by weight Zn, or 0.4 to 0.5% by weight Ca, or both.

\* \* \* \* \*